(12) United States Patent
Guan et al.

(10) Patent No.: US 11,390,915 B2
(45) Date of Patent: *Jul. 19, 2022

(54) POLYNUCLEOTIDE ADAPTER DESIGN FOR REDUCED BIAS

(71) Applicant: New England Biolabs, Inc., Ipswich, MA (US)

(72) Inventors: Shengxi Guan, Stoneham, MA (US); Sean Maguire, Gloucester, MA (US)

(73) Assignee: New England Biolabs, Inc., Ipswich, MA (US)

( * ) Notice: Subject to any disclaimer, the term of this patent is extended or adjusted under 35 U.S.C. 154(b) by 287 days.

This patent is subject to a terminal disclaimer.

(21) Appl. No.: 16/796,113

(22) Filed: Feb. 20, 2020

(65) Prior Publication Data
US 2020/0340050 A1    Oct. 29, 2020

Related U.S. Application Data

(60) Provisional application No. 62/839,191, filed on Apr. 26, 2019.

(51) Int. Cl.
C12Q 1/6855 (2018.01)
C12N 15/10 (2006.01)

(52) U.S. Cl.
CPC ........ C12Q 1/6855 (2013.01); C12N 15/1093 (2013.01); C12N 15/1096 (2013.01); C12Q 2525/191 (2013.01)

(58) Field of Classification Search
CPC ............ C12Q 1/6855; C12Q 2525/131; C12Q 2525/179; C12Q 2525/191; C12N 15/1093; C12N 15/1096
See application file for complete search history.

(56) References Cited

U.S. PATENT DOCUMENTS

| 8,163,479 | B2 | 4/2012 | Jaccard et al. |
| 8,178,314 | B2 | 5/2012 | Kindermann et al. |
| 8,227,602 | B2 | 7/2012 | Gautier et al. |
| 8,975,388 | B2 | 3/2015 | Zichi et al. |
| 2013/0261027 | A1 | 10/2013 | Li et al. |
| 2014/0357528 | A1 | 12/2014 | Robb et al. |
| 2015/0105275 | A1* | 4/2015 | Wong ................... C12Q 1/6855 435/6.12 |
| 2016/0265031 | A1 | 9/2016 | Liu et al. |
| 2017/0145500 | A1 | 5/2017 | Myers et al. |
| 2018/0010178 | A1 | 1/2018 | Charizanis et al. |
| 2019/0194649 | A1 | 6/2019 | Raine et al. |

FOREIGN PATENT DOCUMENTS

WO    2012158603 A2    11/2012

OTHER PUBLICATIONS

Maguire, et al, Nucleic Acids Research, 48, 14, e80.
Wu, et al, BMC Genomics, 19, 1, 1-12, 2018.
Hafner, et al., RNA, 17, 9, 1697-1712, 2011.
Gansauge, et al, Nucleic Acids Research, gkx033, 2017.
Bottani, et al., Journal of Clinical Medicine, 8, 1661 (2019).
Keam, et al., Life 5, 1638-1651 (2015).
Kumar, et al., BMC Biology, 12, 78 (2014).
Shigematsu, et al., Gene Regulation and Systems Biology, 9, 27-33 (2015).
Giraldez, et al., Nature Biotechnology, 36, 8, 476-757, 2018.
Xu, et al., Methods in next generation sequencing, 2, 1-10, 2015.
Yau, et al., The FEBS Journal, 285, 19, 3669-3682, 2018.

* cited by examiner

Primary Examiner — David C Thomas
(74) Attorney, Agent, or Firm — New England Biolabs, Inc; Harriet M. Strimpel

(57) ABSTRACT

Compositions are provided for 3' adapters and methods of use are provided that include methods requiring a plurality of ligation steps involving a single-stranded target polynucleotide and 3' and 5' adapters. Embodiments of the 3' adapters comprise a cleavable linker positioned between a single-stranded region and a double-stranded region. Upon ligating the 3' adapters, the single-stranded region is released by cleaving the cleavable linker.

30 Claims, 10 Drawing Sheets
(4 of 10 Drawing Sheet(s) Filed in Color)
Specification includes a Sequence Listing.

Blockage of 3' end of bottom strand of Adapter 2 increases library yield.

USER cutting before second ligation at 5' end of target RNA decrease adapter-dimer formation and increase Nicking enzymes can be used to cut the bottom strand of Adapter 2 to generate the library Splint ligation method has higher library yield

Percentage of miRNA within 2-fold of Expected Value
Illumina    14.7%
Bioo        38.3%
Splint      84.3%

Splint ligation based RNA library preparation shows less bias

Splint ligation based RNA library preparation shows consistent performance across different RNA input (from 10ng to 1ug)

Modified nucleotides in the 6 degenerated nucleotide region of bottom strand of Adapter 2 increased the library yield.

SEQUENCE LISTING

<160> NUMBER OF SEQ ID NOS: 5

<210> SEQ ID NO 1
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (22)..(24)
<223> OTHER INFORMATION: 3InvdT

<400> SEQUENCE: 1
agatcggaag agcacacgtc tttt                                          24

<210> SEQ ID NO 2
<211> LENGTH: 30
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(21)
<223> OTHER INFORMATION: n at position 21 is ideoxyU
<220> FEATURE:
<221> NAME/KEY: misc_feature
<222> LOCATION: (22)..(22)
<223> OTHER INFORMATION: n at position 22 is a, or t, or g, or c, where
      25 percent of the DNA molecues in the population have a, 25
      percent have t, 25 percent have g and 25 percent have c.
<220> FEATURE:
<221> NAME/KEY: misc_feature
<222> LOCATION: (23)..(27)
<223> OTHER INFORMATION: n is a, c, g, or t

<400> SEQUENCE: 2
agacgtgtgc tcttccgatc nnnnnnnttt                                    30

<210> SEQ ID NO 3
<211> LENGTH: 26
<212> TYPE: RNA
<213> ORGANISM: Artificial Sequence
<220> FEATURE:
<223> OTHER INFORMATION: Synthetic construct

<400> SEQUENCE: 3
guucagaguu cuacaguccg acgauc                                        26

<210> SEQ ID NO 4
<211> LENGTH: 32
<212> TYPE: RNA
<213> ORGANISM: Artificial Sequence

```
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: n at position 1 is a, or t, or g, or c where 25
      percent of the DNA molecues in the population have a, 25 percent
      have t, 25 percent have g and 25 percent have c.
<220> FEATURE:
<221> NAME/KEY: misc_feature
<222> LOCATION: (2)..(6)
<223> OTHER INFORMATION: n is a, c, g, or u

<400> SEQUENCE: 4
nnnnnngauc gucggacugu agaacucuga ac                                       32

<210> SEQ ID NO 5
<211> LENGTH: 35
<212> TYPE: RNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (1)..(6)
<220> FEATURE:
<221> NAME/KEY: misc_feature
<222> LOCATION: (1)..(1)
<223> OTHER INFORMATION: n at position 1 is a, or t, or g, or c where 25
      percent of the DNA molecues in the population have a, 25 percent
      have t, 25 percent have g and 25 percent have c.
<220> FEATURE:
<221> NAME/KEY: misc_feature
<222> LOCATION: (2)..(6)
<223> OTHER INFORMATION: n is a, c, g, or u
<220> FEATURE:
<221> NAME/KEY: misc_feature
<222> LOCATION: (33)..(35)
<223> OTHER INFORMATION: n is t
<220> FEATURE:
<221> NAME/KEY: misc_feature
<222> LOCATION: (33)..(35)
<223> OTHER INFORMATION: n is 3InvdT

<400> SEQUENCE: 5
nnnnnngauc gucggacugu agaacucuga acnnn                                    35
```

POLYNUCLEOTIDE ADAPTER DESIGN FOR REDUCED BIAS

CROSS-REFERENCE

This application claims priority to U.S. Provisional Application No. 62/839,191 filed Apr. 26, 2019, which is hereby incorporate in its entirety by reference.

BACKGROUND

Preferential ligation of adapters to some single-stranded RNAs and not others in an RNA library results in inaccurate profiling of a library composition. In order to reduce bias, adapters having single-strand extensions that act as splints can be utilized. However, such adapters can readily ligate with each other in part because of their excess concentration relative to the target RNA. Adapter-adapter ligation is particularly problematic when the target RNAs are small because the ligation artefacts may not be readily distinguished from target RNAs based on size. As a consequence, standard size separation techniques such as electrophoresis are ineffective. Current methods are thus challenged by low sensitivity and high bias, limiting their ability to capture an accurate representation of the cellular small RNA population. Small RNAs are important regulators of gene expression and are involved in human development and disease. Next generation sequencing (NGS) allows for scalable, genome-wide studies of small RNA.

SUMMARY

Provided herein are adapters that have improved properties including that they generally do not self-ligate but can ligate efficiently to a target polynucleotide such as a target RNA and show reduced bias in binding substantially all RNAs in an RNA library without preference. Examples of adapters include partially double-stranded polynucleotide molecules that can be either DNA or RNA and can be formed from a single polynucleotide strand such as a hairpin or loop structure. Alternatively, the polynucleotide molecule may be formed from two polynucleotide strands. Embodiments of the polynucleotide molecules comprise a top strand and a bottom strand, wherein: the top strand is complementary to a portion of the bottom strand to form a double-stranded region; and the bottom strand has a non-complementary 3' single-stranded extension comprising a sequence of at least 4 degenerate nucleotides that is random and differs for each polynucleotide in a population of polynucleotides and also a site-specific cleavable sequence or nucleotide at or near the junction between the double-stranded region and the single-strand extension, suitable for causing the removal of the single-strand extension by cleavage. Polynucleotide molecules having a 3' single-stranded extension can be used as 3' adapters. The 3' adapters may optionally contain a blocking moiety at the 3' terminus of the bottom strand and/or a phosphorylated or pre-adenylated 5' terminus on the top strand.

Another embodiment provides an adapter suitable for an RNA library that includes a partially double-stranded polynucleotide molecule comprising a double-stranded region having a first nucleic acid strand and a second complementary nucleic acid strand, wherein: (i) the first and second strands are a portion of one or comprise 2 polynucleotide molecules, (ii) the first nucleic acid strand optionally comprises one or more of a phosphorylated or pre-adenylated at the 5' terminus; (iii) the second complementary strand having a nucleic acid sequence that extends 3' from the double-stranded region to form a single-stranded extension containing at least 4 degenerate nucleotides in a sequence wherein the sequence differs for each polynucleotide in a population of polynucleotides; and (iv) a site-specific cleavable sequence or nucleotide at or near the junction between the double-stranded region and the single-strand extension, suitable for removing the single-strand extension by cleavage. The second complementary strand may optionally have a blocking moiety.

In some embodiments, the top strand (or first strand) preferably comprises a pre-adenylated 5' terminus.

In some embodiments, the 3' single-stranded extension has a length in the range of 4-12 nucleotides and the site-specific cleavable sequence or nucleotide is a deoxyuridine.

In some embodiments, the single-strand extension has a length in the range of 4-12 nucleotides and the site-specific cleavable sequence or nucleotide is a restriction endonuclease cleavage site.

In some embodiments, the blocking nucleotide prevents ligation.

In some embodiments, the blocking nucleotide comprises a modification selected from the group consisting of a 3' inverted dT, a 3' C3 spacer, a 3' amino dN, a 3' phosphorylated dN and a dideoxynucleotide.

In some embodiments, the site-specific cleavable sequence or nucleotide is positioned at the junction of the single-stranded extension and the double-stranded region.

In some embodiments, the site-specific cleavable nucleotide or sequence is positioned within the double-stranded region on the bottom strand (or second strand) within 8 nucleotides of the junction of the single-stranded extension and the double-stranded region.

In some embodiments, there is more than one cleavable nucleotide or sequence in the polynucleotide molecule, wherein cleavable nucleotides or sequences are positioned in the double-stranded region on the bottom strand within 8 nucleotides of the junction of the single-stranded extension and the double-stranded region, preferably within 4 nucleotides from the junction.

Also provided is a kit. In some embodiments the kit may comprise (a) a polynucleotide molecule as summarized above suitable for use as a 3' adapter; and (b) a second polynucleotide suitable for use as a 5' adapter comprising a top strand and a bottom strand, wherein the top strand is complementary to a portion of the bottom strand to form a double-stranded region and the bottom strand comprises a 5' single-stranded extension that contains a sequence of at least 4 degenerate nucleotides wherein the at least 4 degenerate nucleotide sequence is a random sequence that differs for each polynucleotide in a population of polynucleotides.

In some embodiments, the kit may further comprise one or more enzymes selected from the group consisting of a ligase, a nicking endonuclease, a glycosylase, a deadenylase, and an exonuclease.

The first and second polynucleotide molecules may be DNA or RNA. In one embodiment, the first polynucleotide is DNA for ligating to the 3' end of a target RNA or DNA and the second polynucleotide is an RNA for ligation to the 5' end of the molecule. In one embodiment, the target polynucleotide is an RNA. In one embodiment the target polynucleotide is a library of RNA molecules such that the adapter ligated RNA library is suitable for sequencing by a sequencing platform. The kit may include instructions for use in methods that require a plurality of ligation steps involving a single-stranded target polynucleotide or a library of small RNA molecules and 3' and 5' adapters for purposes related to at least one of characterization and quantification of the target polynucleotide. Examples of uses of kit include reducing background, which is exacerbated during amplification of a reverse transcript of an RNA, for sequencing reactions (for example NGS or Sanger sequencing), quantification and/or cloning or other uses known in the art.

In one embodiment, a method is provided for ligating 3' adapters to RNA, that includes combining any of the polynucleotide molecules described above with a population of RNA molecules to produce a reaction mix; incubating the reaction mix to ligate the 3' adapter polynucleotide molecule to the 3' of the RNA molecules; and cleaving the polynucleotide molecule at the site-specific cleavable sequence or nucleotide so as to remove the degenerate sequence.

In a further embodiment, the method includes adding a 5' polynucleotide adapter molecule having a 5' single-strand extension comprising degenerate nucleotides to the product of step (c) to produce a second reaction mix; and incubating the second reaction mix to ligate the 5' polynucleotide adapter to the RNA molecules.

In some embodiments, the steps of the method may be performed in a single reaction vessel.

In some embodiments, no intermediate purification or separation steps are performed between steps (a)-(e).

In some embodiments, the method may further comprise incubating the product of step (e) with a reverse transcriptase, to copy the ligated RNA into complementary DNA (cDNA). In these embodiments, cDNA synthesis may be primed using the bottom strand of the polynucleotide molecule, after the 3' single-stranded extension has been cleaved.

In some embodiments, high adapter ligation yield and reduced bias does not vary significantly for other populations of RNA.

In some embodiments, the target RNA molecules in a library are variable in size and concentration.

In any of the above embodiments, reference to the "top" strand is intended to include a reference to the first strand, and reference to the "bottom" strand is intended to include reference to the second strand. Also reference to "degenerate nucleotides" in the polynucleotide molecule refers to a sequence of at least 4 nucleotides wherein the at least 4 degenerate nucleotide sequence is a random sequence that differs for each polynucleotide in a population of polynucleotides. The nucleotides in the degenerate sequence may be selected from A, G, U, T, C and modifications and analogs thereof that may be naturally occurring or unnatural chemical analogs.

BRIEF DESCRIPTION OF THE FIGURES

The patent or application file contains at least one figure executed in color. Copies of this patent or patent application publication with color figures will be provided by the Office upon request and payment of the necessary fee.

The figures and drawings are intended to illustrate one or more versions of the compositions and/or methods described herein. Unless stated otherwise, these are not intended to be limiting for the purpose of interpreting the scope of any claims.

DETAILED DESCRIPTION OF THE EMBODIMENTS

Figure 1:
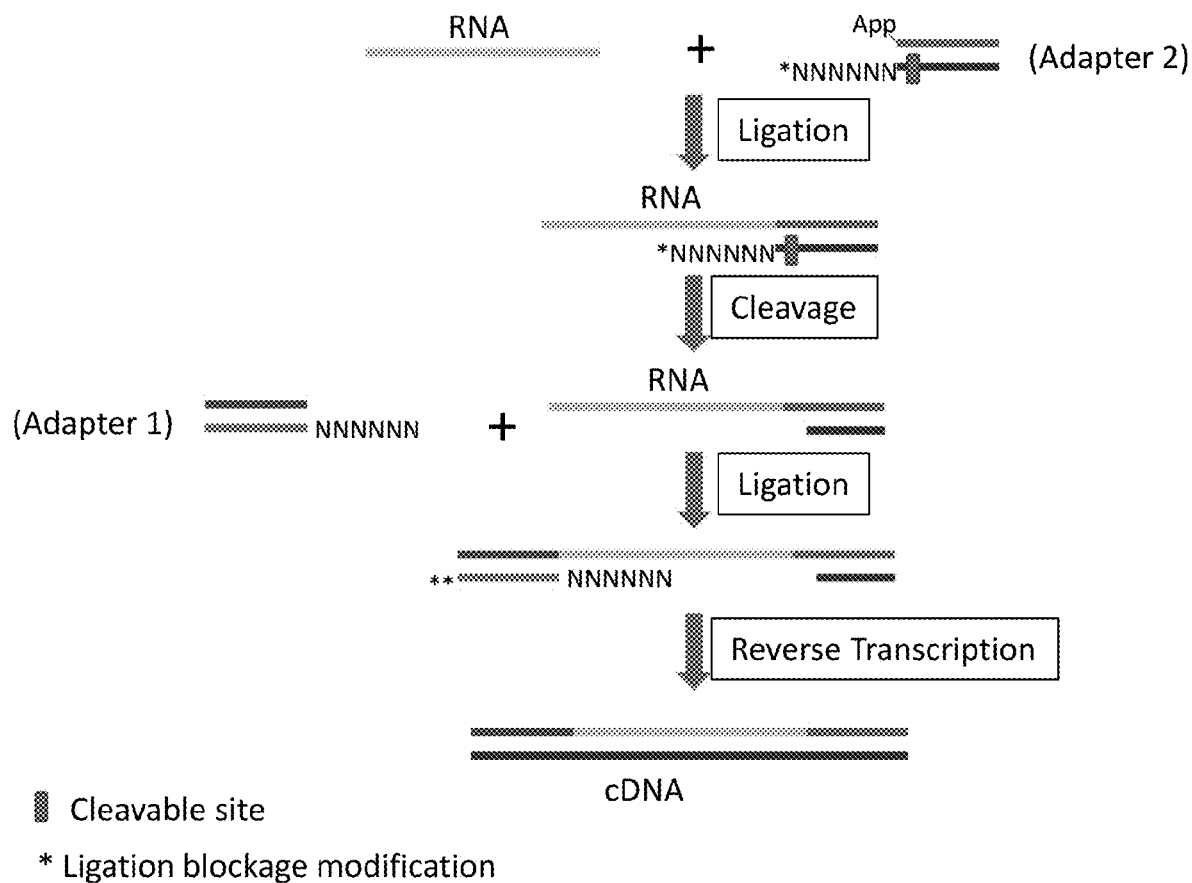
FIG. 1 shows a workflow in which polynucleotide adapter molecules can be added to both the 3' end and the 5' end of a target polynucleotide, including nucleic acids that have unknown ends. This figure illustrates an example in which adapters are ligated to RNAs that do not have a polyA tail. In this example, the workflow involves four steps: (a) ligating one strand of a splinted double-stranded adapter that contains a 3' single-stranded extension (Adapter 2) to the 3' end of a target nucleic acid; (b) removing 3' single-stranded extension of the ligated adapter by cleavage of a site in the adapter; (c) ligating a strand of a double-stranded nucleic acid adapter that contains a 5' single-stranded extension (Adapter 1) to the 5' end of the target nucleic acid; (d) reverse transcribing the product of step (c) to produce cDNA that has adapter sequences at both ends; and (e) optionally PCR amplifying the adapter ligated polynucleotide (not shown). The 3' adapter as shown is characterized by a first top strand and a complementary bottom strand where the bottom strand includes a degenerate 3' single-strand extension and one or more cleavage sites positioned on the bottom strand at the junction of the single-strand or double-strand regions or contained within the double-stranded region on the bottom strand. Other features of the 3' adapter may include a terminal adenylated diphosphate at the 5' terminus of the top strand and a modified terminal nucleotide on the 3' end of the bottom strand. The 5' adapter similarly has a top strand and a complementary bottom strand with the bottom strand having a 5' single-strand extension containing degenerate bases.

Unless defined otherwise, all technical and scientific terms used herein have the same meaning as commonly understood by one of ordinary skill in the pertinent art. Embodiments described herein may include one or more ranges of values (e.g., size, concentration, time, temperature). A range of values will be understood to include all values within the range, including subset(s) of values in the recited range, to a tenth of the unit of the lower limit unless the context clearly dictates otherwise. As used herein, the articles "a", "an", and "the" relate equivalently to a meaning as singular or plural unless the context dictates otherwise.

The term "polynucleotide" refers to a DNA, RNA, chimeric DNA/RNA molecule, or a DNA strand hybridized to an RNA strand. A "polynucleotide" may have one or more modified bases. The term "polynucleotide" as defined herein is used to describe the target and the adapters. Thus, any of the target polynucleotide, 3' adapter and/or 5' adapter may be a DNA, an RNA, or a DNA/RNA chimera or hybrid; and may contain one or more modified nucleotides, for example 2'-O-methyl NTP.

The term "strand" as used herein refers to a nucleic acid made up of nucleotides covalently linked together by covalent bonds, e.g., phosphodiester bonds. Double-stranded DNA has two complementary strands of nucleic acid referred to herein as the "top" and "bottom" strands. The assignment of a strand as being a top or bottom strand (or any of the equivalent terms such as "Watson" and "Crick") is arbitrary and does not imply any particular orientation, function or structure.

The term "degenerate sequence" refers to a region of a polynucleotide in which any nucleotide can occur in preferably a random order. For instance, in a chemically synthesized oligonucleotide, a specific position in the oligonucleotide polymer could be specified to have any nucleotide incorporated. This is achieved by introducing a mixture of nucleotides (most often dA, dG, dC, dT for DNA oligonucleotides, and A, G, C and U for RNA oligonucleotides) during the stepwise chemical reactions that result in oligonucleotide chain elongation. A degenerate sequence may by described by the formula $N_{2-10}$ (e.g., $N_3$-$N_8$), where N corresponds to G, A, C, and T or U, or equivalent modified (e.g. 2'O methylated) nucleotides. A polynucleotide that comprises "at least 4 degenerate nucleotides" thus comprises a sequence of 4 nucleotides, each of which may be N. The length of the degenerate sequence is at least 4, 5, 6, 7, 8, or 9 nucleotides. A degenerate sequence an also be described as a "random" sequence. A degenerate sequence comprises one or more (e.g., at least 2, at least 3, at least 4, at least 5, or 5 to 30 or more) nucleotides selected from R, Y, S, W, K, M, B, D, H, V, N (as defined by the IUPAC code). In other words, a degenerate sequence varies from molecule to molecule. In some, a degenerate sequence may be random (i.e., composed of a series of Ns, where N is represented by all four nucleotides in a population of molecules). An oligonucleotide having a degenerate sequence can be made by mixing together oligonucleotides of a defined sequence or by synthesizing an oligonucleotide such that a mixture of bases is added to one or more positions. The nucleotides in a degenerate sequence may be selected from A, U, G, T and C or modifications thereof or analogs thereof. Examples of modified nucleotides include methylated, hydroxymethylated, or glucosylated nucleotides. Other modifications include 8-oxoguanine and thymidine dimers. Also included are any known chemical modifications including naphthalene modified cytosine (see for example, U.S. Pat. No. 8,975,388) modified benzylguanine (see for example, U.S. Pat. Nos. 8,178,314, 8,163,479, and 8,227,602) and tagged nucleotides such as biotinylated nucleotides.

"Ligating," as used herein, refers to joining of separate single-stranded polynucleotides to each other to form a single molecule. This is commonly but not exclusively achieved by means of a ligase. An RNA ligase can readily ligate a single-strand DNA to a single-strand RNA at the 3' end of the RNA. An RNA ligase can also readily ligate a 5' end of an RNA to a 3' end of an RNA. The ligation reactions described herein are generally achieved by means of a ligase such as available commercially and described in the New England Biolabs, Inc. catalog. Ligases include ATP-requiring RNA ligases such as a T4 RNA ligase 1 and T4 RNA ligase 2 such as T4 Ligase 2 truncated KQ or other mutants of T4 RNA ligase 2 as described in the examples and additionally include NAD requiring ligases such as Taq ligase. Another alternative ligase is Chlorella virus PBCV-1 ligase for splint ligation. Splint ligation may be achieved when 2 single-strand polynucleotide molecules anneal at proximate positions on a single complementary 'splint" molecule (single-stranded polynucleotide) and ligation occurs at the proximate ends of the two adjacent single-stranded polynucleotides.

Provided herein is a 3' adapter, i.e., a polynucleotide molecule suitable for ligating to the 3' end of a single-stranded target polynucleotide. In some embodiments, the 3' adapter may be used in conjunction with a 5' adapter to make cDNA from a population of RNA molecules. In some embodiments, the features of these adapters include, for the 3' adapter, a cleavable single-stranded degenerate sequence (which can be used as a "splint" during ligation) and blocking groups. When the adapters are ligated to a population of RNA molecules, the 3' adapter may be DNA while the 5' adapter may be RNA or a hybrid DNA/RNA, where the degenerate sequence is DNA. Individual adapters that include the degenerate sequence are generally at least 4-10 or more nucleotides and preferably less than 100 nucleotides, 50 nucleotides or 30 nucleotides in length.

The target polynucleotide may be a single species derived from nature or may be synthetic or may be part of a library where the members of the library are derived from a cell or genome or other source.

Where the target polynucleotide is an RNA, the RNA may include micro RNAs (miRNAs), PIWI associated RNAs (piRNAs), short interfering RNAs (siRNAs), endogenous short interfering RNAs (esiRNAs) and short hairpin RNAs (shRNAs). Messenger RNA (mRNA), fragments of mRNA, viral RNA and structural RNAs like ribosomal RNA (rRNA), transfer RNA (tRNA) and 5S ribosomal RNA (5S RNA) can all be ligated and amplified by this approach. There are no size or sequence requirements for the polynucleotide. However, the polynucleotide preferably has a free 3' OH to allow its' ligation to a 3' adapter.

The 3' adapter includes a double-stranded region (of e.g., 4-50 bp, e.g., 8-30 bp, e.g. about 20 bp), that has a top strand and a bottom strand. The 5' terminus of the top strand may be phosphorylated or adenylated or have other chemical moieties on the 5' terminus that facilitates bimolecular ligation. No blocking group is necessary on the 3' end of the top strand. The 3' adapter molecule has a blocking nucleotide on the 3' terminus of the bottom strand. The blocking nucleotide has, for example, a modified deoxyribose or ribose sugar, such that the 3'hydroxyl group is unavailable for further extension of the oligonucleotide by 3' to 5' phosphodiester formation. Examples of ligation blocking modifications include 3' inverted dT, 3' C3 spacer, 3' amino, 3' phosphorylation, and dideoxynucleotides. Generally, the modification prevents the 3' end from ligating, i.e., makes the 3' hydroxyl group unavailable for 3' to 5' phosphodiester bond formation.

The 3' single-stranded extension (the "splint" region) on the bottom strand is joined to the double-stranded region by a junction region, which may be a nucleotide, linker or other sequence. The single-stranded extension of degenerate nucleotides that forms the splint has a length that is, e.g., at least 4 nucleotides, 5 nucleotides, 6 nucleotides, 7 nucleotides, 8 nucleotides or 9 nucleotides, although 6 nucleotides are exemplified in the figures. The sequence of the single-stranded region may vary in a pool of adapters used to create a single library. The amount of sequence variation may depend on, for example, the length of the degenerate sequence and the number of different nucleotides that are permitted at each position.

In one embodiment, the single-strand extension on the bottom strand of a DNA adapter is hybridized to a target single-strand RNA. Subsequent ligation of the 3' end of the target RNA and the 5' end of the top strand of the DNA adapter occurs to form a double-stranded region. The single-strand extension on the adapter is then removed by cleavage. Cleavage preferably occurs at a single site located at or within 5 or 8 nucleotides from the junction region between the double-strand and single-strand regions. In certain embodiments, 1 nucleotide or at the junction is preferable. A plurality of cleavage sites may be introduced into the bottom strand for the purpose of removing the single-strand extension, but one site is sufficient. The DNA adapter may be a 3' adapter for the target polynucleotide.

The cleavage reaction may result from the action of an enzyme or enzyme mix such as a glycosylase/lyase or glycosylase mix to cleave a single nucleotide at the junction; by a nicking endonuclease at a specific sequence; by using by chemical means; by photocleavable means; or a mixture of these methods. In one example, the cleavable site is a single nucleotide (deoxyuridine), and the splint region is released using uracil deglycosylase and an AP endonuclease (e.g. USER®, New England Biolabs, Ipswich, Mass.). In another example, the cleavable site is a sequence containing a cleavage site for a site-specific nicking endonuclease. The recognition sequence for this nicking endonuclease may be present in the double-stranded region of the adapter. Alternatively, the recognition site may be the same as the cleavage site where nicking occurs after a double-stranded molecule is formed between the splint and the target polynucleotide in the reaction mixture. The product of cleavage provides a 3' end for template-dependent polymerase reactions.

For library construction as shown in FIG. 3A-3D, it may be desirable to use a 5' adapter in a second ligation step for ligation to the 5' end of the single-strand target polynucleotide.

The 5' adapter may be DNA but is preferably an RNA or an RNA/DNA hybrid. The 5' adapter comprises a double-stranded region having a top strand (RNA) and a bottom strand (DNA or RNA) with a single-stranded extension (the splint region) at the 5' end. In one embodiment, the single-stranded extension has a length of at least 4 nucleotides, at least 5 nucleotides, at least 6 nucleotides, at least 7 nucleotides at least 8 nucleotides or at least 9 nucleotides although 6 nucleotides are shown in the figures. However, for the 5' adapter, a specific junction nucleotide or sequence is not required, as cleavage of the splint region is not required; nor is a blocking nucleotide required at either end of the bottom strand, since ligation occurs only between the OH on the 3' end of the top strand and the phosphate on the 5' end of the RNA.

The 3' and 5' adapter molecules find utility for those reactions that require attachment of known sequences to both ends of a single-stranded target polynucleotide. The adapter sequences may contain a sample barcode, a unique molecular identifier, priming sites for amplification and sequencing, and/or modifications or labels such as biotin or other label known in the art which enhance separation or identification of adapter-target constructs.

The 3' adapter is suitable for template switching workflows where the addition of a 5' adapter shown in FIG. 1 is substituted by a template switching step for preparing sequencing libraries. The attachment of a 3' adapter to the 3' end of any target RNA is particularly advantageous when the target RNA lacks a known 3' terminus such as a polyA tail. The 5' adapter can optionally be added by template switching.

In addition to providing a primer for reverse transcription, the 3' adapter may be used as an affinity tag to enrich for cell RNA against a background of DNA, protein, lipids, carbohydrates etc. The ligation of the 5' adapter to the 5' end and/or the 3' adapter at the 3' end of the RNA may facilitate sequencing the RNA directly using the Oxford Nanopore platform.

After the adapter sequences have been attached, the RNAs may be converted to cDNA; optionally amplified, and/or sequenced by a variety of methods. Alternatively, for small RNAs, the adapter ligated RNA may be sequenced directly, for example using an Illumina sequencing platform.

Advantages of present embodiments of the method for adapter ligation to any RNA for manufacture of a cDNA using reverse transcriptase include one or more of the following: a one pot workflow; no purification steps required, high yield of a sequencing library formed from RNA; reduced bias; consistency of performance; suitability for single-stranded DNA and single-stranded RNA target polynucleotides having a wide range of sizes and at a wide range of concentrations. For example, sizes of target polynucleotide may range from 20 nucleotides in length to 10 kb or longer dependent on the polymerase used to copy the polynucleotides between the adapters.

The target polynucleotide may be a single-stranded target RNA such as a single intact or fragmented species derived from nature or may be synthetic or may be part of a pool of different types of RNA where the members of the library are derived from a cell or genome or other source such that the members of the library vary in their sequences.

The method described herein can be employed to analyze RNA (particularly small RNAs, long non-coding RNAs or fragmented mRNA) from virtually any organism and/or sample-type originating from prokaryotes, eukaryotes, mycoplasma and archaea. Examples include, but are not limited to, microbes, plants, animals (e.g., reptiles, mammals, insects, worms, fish, etc.), tissue samples, cadaveric tissue, archaeological/ancient samples, etc. In certain embodiments, the RNA sample used in the method may be derived from a mammal, where in certain embodiments the mammal is a human. In exemplary embodiments, the RNA sample may contain RNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the RNA sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, and semen. In particular embodiments, a sample may be obtained from a subject, e.g., a human. In some embodiments, the sample analyzed may be a sample of cell-free RNA (cfRNA) obtained from blood, e.g., from the blood of a pregnant female or a patient such as a cancer patient. In other embodiments, the sample may be a pathogenic organism, sample from a microbiome, a plant sample or a fungal sample where the RNA to be sequenced is diagnostic for a selected situation such as disease, barcode of life, or phenotype analysis in a population of a single species.

The adapters and their use in a library preparation process using randomized splint ligation resolves previous challenges reducing bias and sensitivity of sequencing associated with this ligation strategy. The randomized splint ligation-based workflow described herein can reduce bias and increase the sensitivity of small RNA sequencing for a wide variety of target RNAs such as small RNAs, 2' OMe modified RNA, pseudouridine modified RNA, large RNAs and DNA allowing for highly accurate RNA sequencing. The workflow described herein is suitable for detecting differentially expressed small RNAs (18-33 nucleotides) that have a fundamental role in transcriptional and post-transcriptional gene regulation and can be used diagnostically, for example, in tumor and matched normal tissues analysis.

Typically, sRNAs associate with members of the Argonaut protein family to form ribonucleoprotein complexes and act as guides for targeted RNA silencing through complementary base-pairing 1. sRNA based RNA silencing regulates a wide variety of biological processes including development, maintenance and determination of cell fate, fine tuning of gene expression, silencing of transposons and antiviral defenses. Furthermore, aberrant expression of sRNAs are involved in many human diseases. miRNAs in particular are often aberrantly expressed in tumor cells and are useful biomarkers for both diagnosis and prognosis in a variety of cancer types (Bottani, et al., Journal of Clinical Medicine, 8, 1661 (2019)). tRNA fragments are a newly discovered and important class of sRNAs. tRFs are organized into two main categories: longer tRNA-halves and shorter tRNA fragments. Longer 3' and 5' tRNA-halves have a role in regulating protein synthesis and their biogenesis is triggered by cellular stress such as infection, oxidative or nutritional stress (Keam, et al., Life, 5, 1638-1651 (2015)). Less is known about shorter 3'-tRFs and 5'-tRFs, however it has been shown that they can be loaded onto Argonauts and guide mRNA silencing on a variety of targets using mechanisms similar to miRNA induced silencing (Kumar, et al., BMC Biology, 12, 78 (2014) and Shigematsu, et al., Gene Regulation and Systems Biology, 9, 27-33 (2015)).

Figure 9:
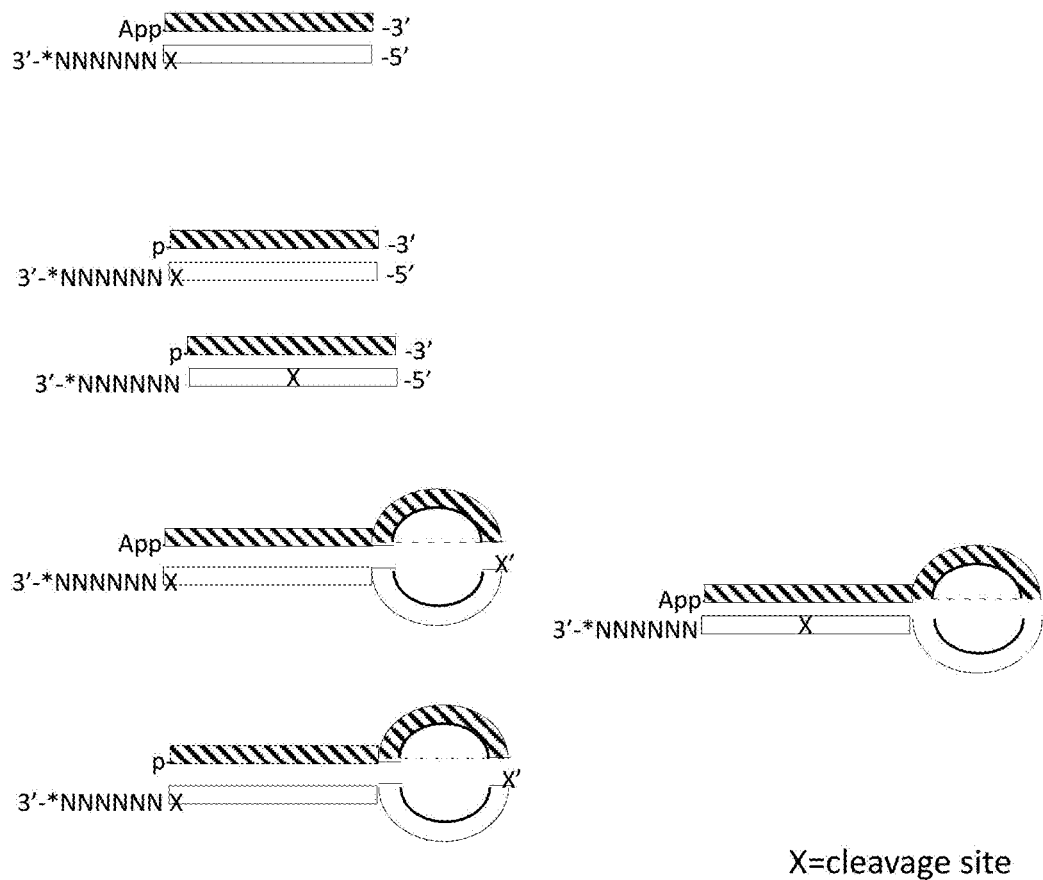
FIG. 9 shows some different forms of the 3' adapter (Adapter 2). "App" or "p" at the 5' terminus of the top strand is adenylation or phosphorylation, respectively. "X" is the site-specific cleavage site. "*" at the 3' terminus of the bottom strand is a blocking nucleotide.

Also provided by this disclosure is a kit for practicing the subject method, as described above. A subject kit may contain at least a 3' adapter of the invention (e.g. as described in FIG. 9). The kit may further comprise a 5' adapter as described above; and/or the kit may also contain one or more enzymes, such as a ligase, a deadenylase, a glycosylase/lyase, and/or a nicking endonuclease.

The kit may include instructions for use in methods that require a plurality of ligation steps involving a single-stranded target polynucleotide and 3' and 5' adapters for purposes related to at least one of characterization and quantification of the polynucleotide. Examples of uses of the kit include sequencing of small RNAs (21-23 nucleotides) that are used by cells in genome regulation and can also be used as biomarkers. Other uses include sequencing RNA fragments in blood. Small RNA molecules can be sequenced directly by Illumina sequencing platforms and do not require reverse transcriptases for analysis. Because the RNAs are small, there is no suitable internal location for priming synthesis of complementary strands, hence the adapters provide external priming sites for this purpose.

Examples of uses of kit include reducing background, which is exacerbated during amplification of a reverse transcript of an RNA, for sequencing reactions (for example NGS or Sanger sequencing), quantification and/or cloning or other uses known in the art.

The components of the kit may be combined in one container, or each component may be in its own container. For example, the components of the kit may be combined in a single reaction tube or in one or more different reaction tubes. Further details of the components of this kit are described above. The kit may also contain other reagents described above and below that are not essential to the method but nevertheless may be employed in the method, depending on how the method is going to be implemented.

In embodiments of the invention, the polynucleotide described herein having a top strand and a bottom strand are not naturally occurring.

The term "non-naturally occurring" refers to a nucleic acid that contains: a) a sequence of nucleotides that is different to a nucleic acid in its natural state (i.e. having less than 100% sequence identity to a naturally occurring nucleic acid sequence), b) one or more non-naturally occurring nucleotide monomers (which may result in a non-natural backbone or sugar that is not G, A, T or C) and/or c) may contain one or more other modifications (e.g., an added label or other moiety) to the 5'- end, the 3' end, and/or between the 5'- and 3'-ends of the nucleic acid.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

All publications, patents, and patent applications mentioned in this specification are herein incorporated by reference to the same extent as if each individual publication, patent, or patent application was specifically and individually indicated to be incorporated by reference.

EXAMPLES

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Example 1: Splint Ligation for Generating an RNA Sequencing Library in a Single Reaction Vessel In this example, the input RNA was a pool of microRNAs that contained 962 synthetic miRNA with equimolar concentration (the MiRXplore library from Miltenyi Biotec, (Auburn, Calif.). All total RNA samples were obtained from BioChain, Inc. (Newark, Calif.). All oligonucleotides were synthesized by Integrated DNA Technologies, Inc. (Coralville, Iowa). A DNA adapter was first ligated to the 3' end and then an RNA adapter was ligated to the 5' end of each input RNA in the pool using the workflow shown in FIG. 1, to form a sequencing library. The 5' RNA adapter (double-stranded molecule with 5' single-stranded extension) could be substituted with an RNA hybrid, in which the RNA is the top strand suitable for hybridization to the 5' end of the target RNA using T4 RNA ligase and the bottom strand could be DNA or RNA.

To reduce the secondary structure of input RNA, the RNA was heated to 70° C. and then rapidly cooled down on ice. The input RNA (pooled miRNA) (50 fmol) was then ligated to the 3' adapter (Adapter 2) using T4 RNA Ligase 2, Truncated KQ (NEB M0373) by incubating the reaction mix for 1 hour at 25° C. The bottom strand of Adapter 2 was cleaved at the deoxyU with Uracil-DNA Glycosylase (NEB M0280) and Endonuclease IV (NEB M0304). The 5' adapter (Adapter 1) was then added to the reaction and ligated to the 5' end of target RNA with the T4 RNA ligase 2. Protoscript® II Reverse Transcriptase (NEB M0368) was then added to the reaction mix to elongate the bottom strand of Adapter 2 to form the cDNA. Resulting cDNA was then purified using NEBNext® Sample Purification Beads (NEB E7767). The purified cDNA was PCR amplified with Q5® DNA Polymerase (NEB M0491). The PCR products were purified with NEBNext Sample Purification Beads (NEB E7767). The yield of the library was determined by Bioanalyzer® 2100 (Agilent, Santa Clara, Calif.). The sequencing of the library was performed on MiSeq® or NextSeq® platform (Illumina, San Diego, Calif.).

2.5 pmol was used for the 3' adapter and subsequently 5 pmol was used for the 5' adapter.

The sequences of the 3' and 5' adapters are as follows:

```
3' adapter: Adapter 2:
Top strand:
                                        (SEQ ID NO: 1)
/5 App/AGA TCG AAG AGC CAC ACG TCT/3InvdT/

Bottom strand:
                                        (SEQ ID NO: 2)
AGA CGT GTG CTC TTC CGA TC/ideoxyU/ (N1:25252525)

(N1)(N1)(N1)(N1)(N1) /3InvdT/

5' adapter: Adapter 1
Top strand:
                                        (SEQ ID NO: 3)
rGrUrCrArGrArGrUrUrCrUrArCrArGrUrCrCrGrArCrGrArU rC
```

```
Bottom strand:
                                        (SEQ ID NO: 4)
(rN1:25252525)(rN1)(rN1)(rN1)(rN1)(rN1)rGrArUrCrGr UrCrGrGrArCrUrGrUrArGrArArCrUrCrUrGrArArC
```

Adapter 1 and 2 were synthesized by IDT (Coralville, Iowa).

Where preadenylation was used, the 3' and 5' adapters were resuspended in annealing buffer (50 mM NaCl, 10 mM Tris HCl, 0.1 mM EDTA, pH 7.5). The adapter strand of the 3' adapter was pre-adenylated using the 5'DNA Adenylation Kit (NEB E2610) and purified using the Monarch® DNA Cleanup Kit (NEB T1030).

Reverse transcription was performed by adding 50 mM final concentration of Tris-HCl buffer (pH 7.5), 75 mM final concentration of potassium chloride, 10 mM final concentration of DTT, 500 μM final concentration of each DNTP, 20 units of Murine RNase Inhibitor (M0314), 200 units of Protoscript II Reverse Transcriptase (NEB M0368) and nuclease free water to bring the final volume to 50 μL. This reaction was then incubated for 1 hour at 42° C. First strand cDNA products were purified using 70 μL NEBNext Sample Purification Beads (NEB E7767) and 70 μL of 100% Isopropanol. Reactions were washed and eluted in 10 μL of nuclease free water according to the manufacturer's directions (also see FIG. 1).

PCR amplification of the library was performed using NEBNext High-Fidelity 2X PCR Master Mix (NEB M0541) and 25 pmol each of the forward and reverse primers. PCR was performed with the following program: An initial denaturation of 98° C. for 30 seconds followed by a varying number of cycles depending on input of: 98° C. for 10 seconds, 62° C. for 30 seconds and 72° C. Followed by a final elongation step of 72° C. for 5 minutes. Libraries were size selected using the NEBNext Sample Purification Beads (NEB E7767) and using the Small RNA Library Size selection protocol from the NEBNext Small RNA Library Kit (NEB E7330). Purified libraries were assayed on the Agilent 2100 Bioanalyzer to assess purity and concentration before being pooled and sequenced using 50 cycles of single-end Illumina sequencing.

Figure 2:
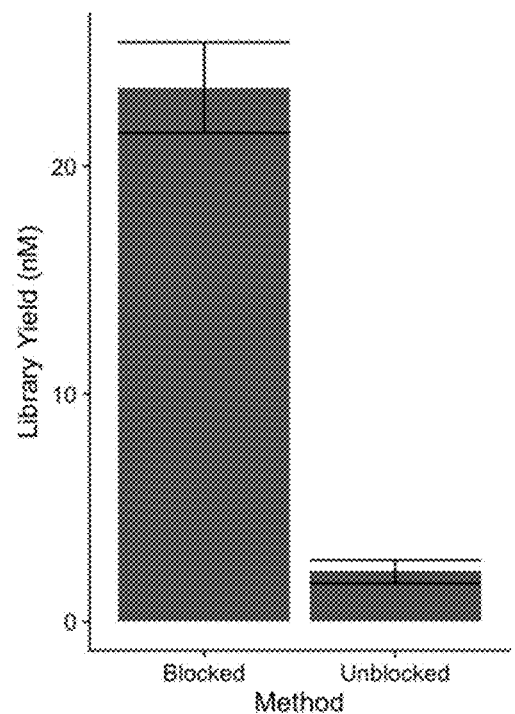
FIG. 2 shows that library yield is enhanced by the workflow exemplified in FIG. 1, where the 3' end of the bottom strand of the 3' adapter (Adapter 2) is blocked from ligation by a modified nucleotide.

To evaluate the effect of a blocking modification on the 3' end of the bottom strand of Adapter 2, an inverted dT blocking group was added. The control was unmodified (Adapter 2 obtained from IDT). This adapter was used according to the method above resulting in an enhancement of the library yield. The library yield using the blocking nucleotide was 10 times more than the one without blocking modification (see FIG. 2).

Figure 5:
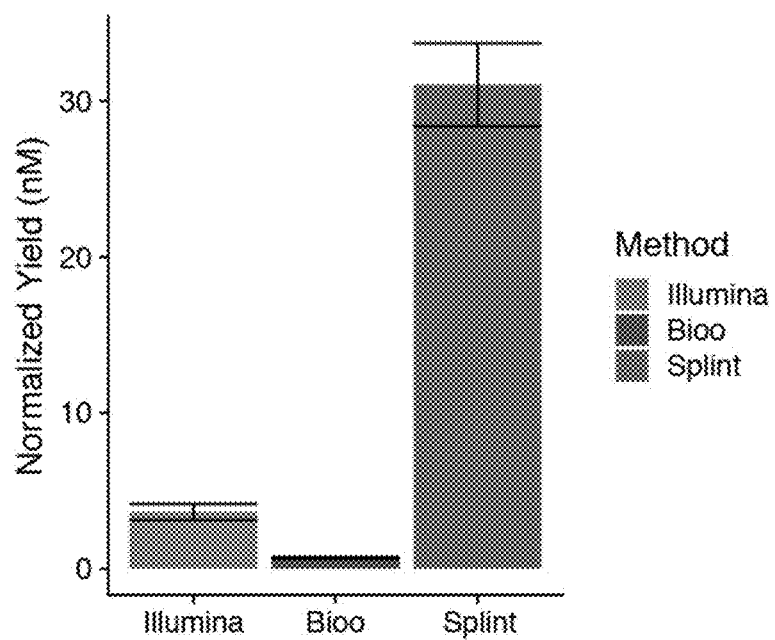
FIG. 5 shows that the yield of library RNA using the workflow in FIG. 1 (splint ligation) is significantly greater than the yield provided by commercially available methods from Illumina and Bioo Scientific.
Figure 6:
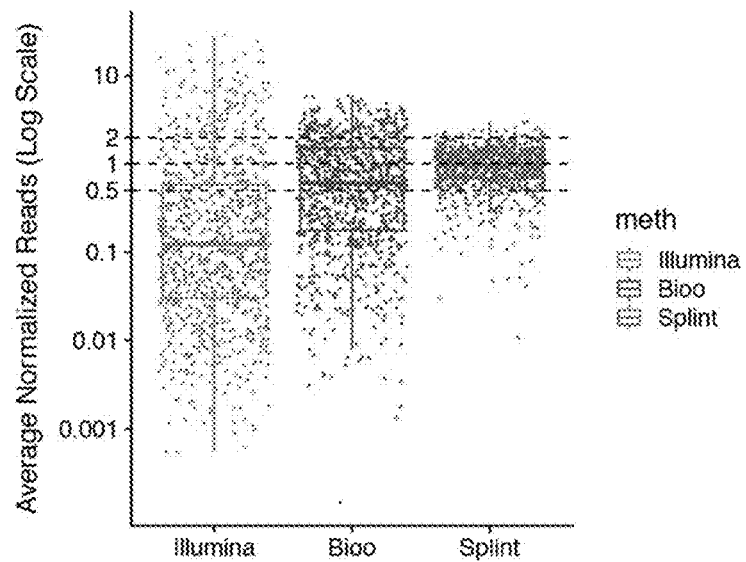
FIG. 6 shows that there is a significant reduction in bias using the workflow described in FIG. 1 compared to the commercially available methods.

Example 2: Splint Ligation Generates Improved Library Yield from Human Brain Total RNA Three different methodologies were compared for constructing RNA libraries using the same amount of starting material (500 ng of human brain total RNA). These were 1) Illumina TruSeq® Small RNA Library Preparation Kits (RS-200-0012, Illumina, San Diego, Calif.), 2) Bioo Scientific NEXTflex® Small RNA-seq Kit V3 (NOVA-5132-05, Bioo Scientific, Austin, Tex.), and 3) the splint ligation-based RNA library preparation method described in Example 1. Libraries were made according to the manufacturer's instructions. Library yield was assessed with the Bioanalyzer. Data shown is the average of 6-8 technical replicates. The yield was normalized to 9 PCR cycles. As a result, the splint ligation-based RNA library preparation method generates higher yield than both Illumina and Bioo Scientific's methods (see FIG. 5).

Figures 3A, 3B:
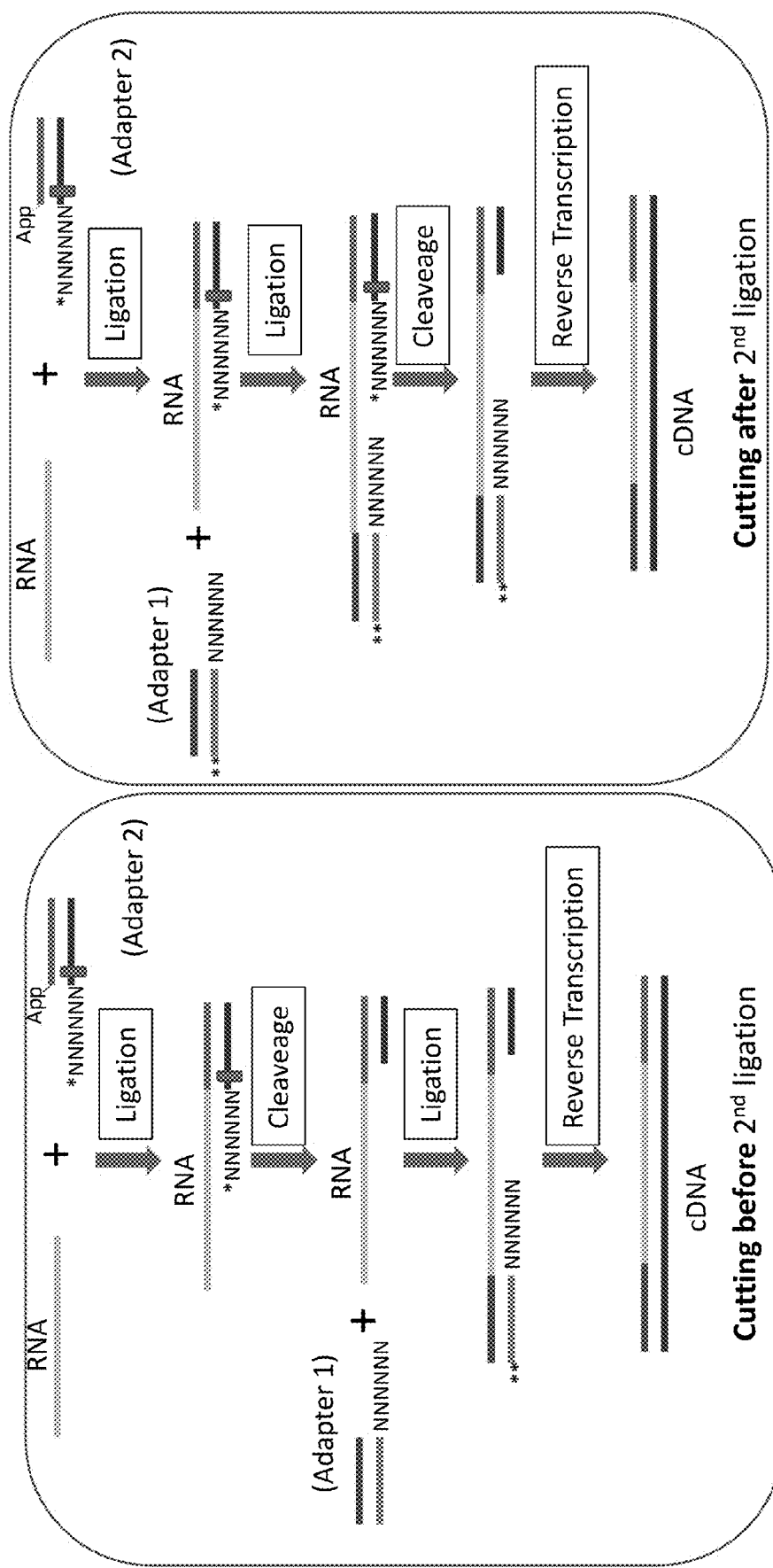
FIG. 3A-3B shows cleavage of the 3' single-strand extension at different stages in two workflows (FIG. 3A ("cut before" second ligation) and FIG. 3B ("cut after" second ligation) and FIG. 3C-3D show the effect of the different work flows on primer dimer formation (FIG. 3C) and on yield of 3' adapter ligated miRNA (FIG. 3D). In the workflow of FIG. 3A the 3' single-strand extension is cleaved before the second ligation step whereas in the workflow of FIG. 3B the 3' single-strand extension is cleaved after the second ligation. In both workflows, the 3' terminal nucleotide of the bottom strand of Adapter 2 is blocked (an optional feature for blocking any residual self ligation).
Figure 3C:
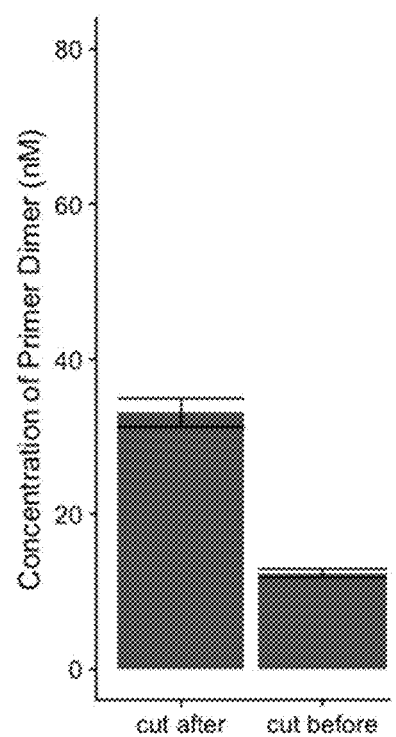
Figure 3D:
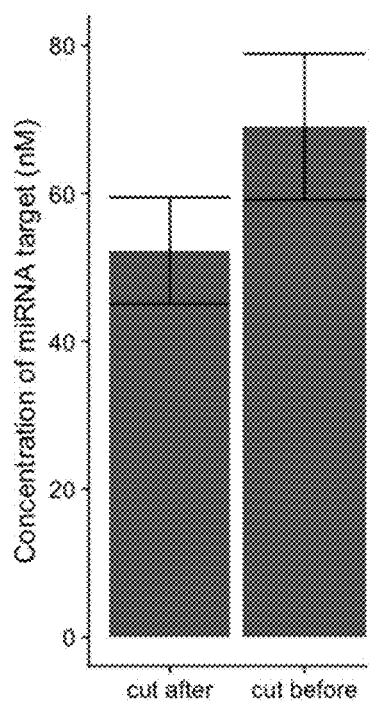

Example 3: To Demonstrate the Benefit of Cleaving the 3' Single-Strand Extension on the 3' Adapter Before the Second Ligation Step RNA libraries were generated as described in Example 1 where the cleavage site in the 3' adapter was deoxyuridine with cleavage using USER to remove the single-strand extension on the bottom strand. Input RNA: 50 fmol of miRXplore™ (Miltenyi Biotech, Bergisch Gladbach, Germany) input RNA and 2.5 pmol Adapter 2 were ligated. Cleavage was done before the second ligation ("cut before") or after the second ligation ("cut after") in which 5.0 pmol Adapter 1 was ligated to the 5' end of the RNA. The results are shown in FIG. 3C. Where USER cleavage was performed before the second ligation, primer dimer formation was decreased while the target miRNA yield was enhanced, when compared with USER cleavage after the second ligation. When the resulting libraries from the two methods were compared, cleavage before the second ligation resulted in a target to adapter dimer ratio of 7:1, whereas cleavage performed after the second ligation produced a ratio of 1.5:1 target to adapter dimer (FIG. 3C) demonstrating the advantages of cleavage of the single-strand extension prior to the second ligation step.

Figure 4:
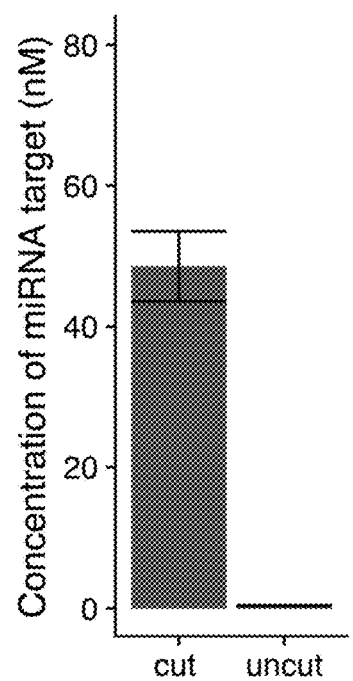
FIG. 4 shows that when the nicking enzyme (Nt.BsmAI in this example) cleaves the single-stranded extension from the 3' adapters after the first ligation of the 3' adapter, the concentration of adapter ligated target RNA increases.

Example 4: To Demonstrate Improved Yield After Cleavage of the Single-Strand Extension Compared with No Cleavage In this example, a nicking endonuclease cleavage site was located in the bottom strand of adapter 2 with a nicking endonuclease recognition sequence in the double-stranded region of the adapter to remove the single-strand extension on Adapter 2 after ligation. The bottom strand of Adapter 2 was designed to contain a BsmAI nicking site for cleaving the single-strand extension. Libraries were made according to the method in Example 1 where 50 fmol of miRXplore were ligated with 2.5 pmol Adapter 2 followed by cleavage with 5 U Nt.BsmAI (NEB R0121), identified in FIG. 4 as "cut" and in the absence of cleavage as "uncut". Subsequently 5.0 pmol Adapter 1 was added to the mixture and ligated to the 5' end of the RNA-adapter conjugate. The yield of RNA library was substantial with the nicking enzyme cleavage, while there were almost no libraries formed in the absence of cleavage of the single-strand extension (FIG. 4).

Figure 7:
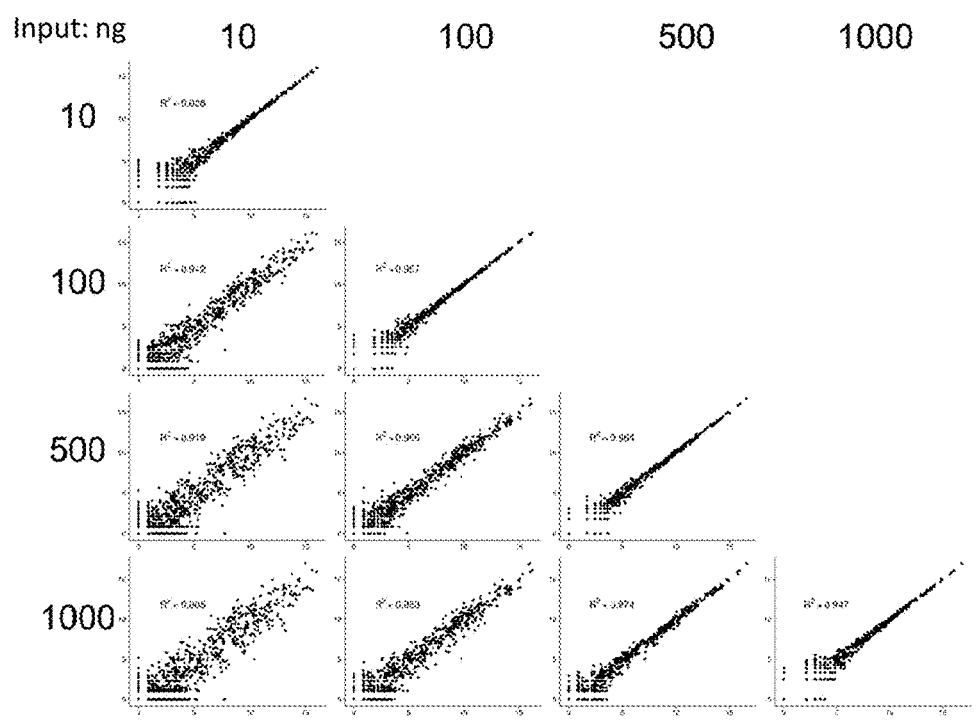
FIG. 7 shows that the workflow in FIG. 1 provides consistent performance over the range of RNA concentrations tested (in the range of 10-1000 ng target RNA sample).

Example 5: Sequencing the Libraries of mcroRNA Showed Reduction of Bias Compared Commercial Kits Sequencing libraries were generated from 50 fmol input of miRXplore Universal Reference RNA as described in Example 1 with three different workflows described in Example 2 to determine the extent of unwanted bias from the adapter ligation reaction. Libraries were sequenced on the Illumina MiSeq in single end mode for 50 cycles to a read depth of greater than 2 million reads per library. Each library was sequenced in duplicate. Datasets were then randomly down-sampled to a depth of 2 million reads for analysis. After adapter trimming, reads were counted by mapping them to the reference sequences provided by the manufacturer. Reads were normalized by dividing the total number of mapped reads in each library by 962 to give an expected read count per miRNA species. Then the read count for each miRNA was divided by the expected read count to give a normalized read count. A miRNA that is present in the expected amount will have a normalized read count of one. Overrepresented sequences will have a normalized read count greater than one and underrepresented sequences will have a normalized read count less than one. Reads were plotted on a log scale. All analysis was done using the BBTools package (https://jgi.doe.gov/data-and-tools/bbtools/). The library generated with the Illumina workflow had the largest bias consisting of a large number of reads that are underrepresented. The library formed using the Bioo Scientific method workflow also showed has a large bias. On the other hand, the splint ligation method has the smallest bias (FIG. 7).

The bias was quantified by the percentage of miRNA sequences that are within 2-fold of the expected value of 1. Sequencing libraries made with the Illumina Kit quantify only 20% of the miRNAs within 2-fold of the expected value, while the Bioo Scientific Kit had 38.3% and the splint ligation method had 84.3% (FIG. 7).

Example 6: The 3' Adapter Ligation Workflow is Consistent for a Wide Range of Input RNA Concentrations Libraries were prepared from 1000, 500, 100 and 10 ng input of total human brain RNA (single healthy male donor, Biochain, Newark, Calif.). Library preparation protocol was stated in Example 1 and was identical for each input level, except for the following changes: Both adapters were diluted for the lower input levels (10-fold for the 100 ng input and 100-fold for the 10 ng input). In addition, the number of PCR cycles was varied according to the RNA input amount (10, 11, 14 and 18 cycles for the 1000, 500, 100 and 10 ng input levels respectively).

For 1000 ng and 500 ng of input RNA, 2.5 pmol was used for the 3' adapter and subsequently 5 pmol was used for the 5' adapter. For 100 ng of input RNA, the adapters were diluted 1:10 (0.25 pmol for the 3' adapter and 0.5 pmol for the 5' adapter). For 10 ng, the adapters were diluted 1:100 (25 fmol for the 3' adapter, 50 fmol for the 5' adapter).

Libraries were sequenced in duplicate on an Illumina MiSeq in single end mode for 50 cycles and down-sampled to a read depth of 2 million. Reads were mapped to the human genome (build GRCh38) using the STAR aligner and quantified using the standard Encode pipeline. Read counts were then log transformed and correlated across input amounts in R (R-project.org) using standard linear regression. The splint ligation-based RNA library preparation methods show consistent performance across different RNA input. Even for the comparison between 10 ng and 1000 ng, the $R^2$ value is more than 0.9, suggesting a high correlation and reflecting a consistent performance of the method across a wide range of input (FIG. 7).

Figure 8:
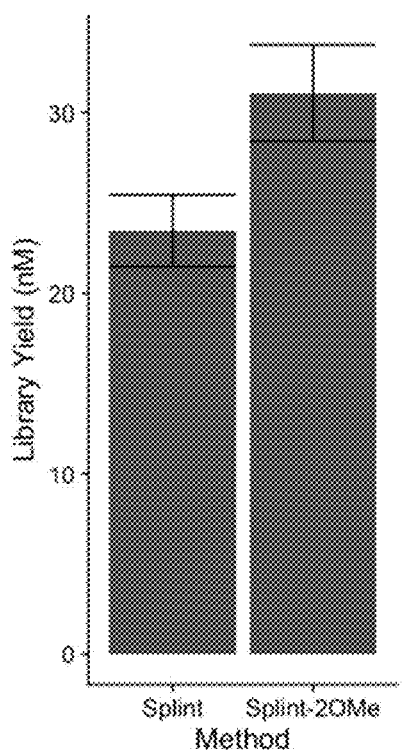
FIG. 8 shows that the performance of the workflow in FIG. 1 can be further enhanced by the substitution of A/G/T and C by 2-Ome A/G/T/C in the degenerate sequence of the 5' single-strand extension of the 5' adapter.

Example 7: Splint Ligation can be Further Improved by Substituting NTP with 2'O-Methylated Nucleotides in the 5' Adapter Single-Strand Extension The 6 degenerate nucleotide region of bottom strand of the 5' adapter (Adapter 1) was designed to contain 6×2'-O methylated nucleotides (SEQ ID NO:3). (IDT) Libraries were made according to Example 1 with 500 ng of total human brain RNA (input RNA), 2.5 pmol Adapter 2 and 5.0 pmol Adapter 1. The yield obtained with modified Adapter 1 was compared with normal Adapter 1. The results showed that the modified nucleotides caused an increase in the library yields (FIG. 8).

3' Adapter 2:
Top strand:
(SEQ ID NO: 1)
/5 App/AGA TCG AAG AGC ACA CGT CT/3InvdT/

Bottom strand:
(SEQ ID NO: 2)
AGA CGT GTG CTC TTC CGA TC/ideoxyU/ (N1:25252525)

(N1)(N1)(N1)(N1)(N1) /3InvdT/

5' Adapter 1
Top strand:
(SEQ ID NO: 3)
rGrUrUrCrArGrArGrUrUrCrUrArCrArGrUrCrCrGrArCrGrArU rC Modified bottom strand:
(SEQ ID NO: 5)
(mN1:25252525)(mN1)(mN1)(mN1)(mN1)(mN1)rGrArUrCrGr UrCrGrGrArCrUrGrUrArGrArArCrUrCrUrGrArArC/3InvdT/

---

What is claimed is:

1. A composition comprising: a partially double-stranded polynucleotide molecule having a top strand and a bottom strand, wherein:

(a) the top strand comprises a nucleic acid sequence that is complementary to a portion of the nucleic acid sequence of the bottom strand, such that the top strand and bottom strand form a double-stranded region by complementary base-pairing; and (b) the bottom strand comprises: (i) a non-complementary 3' single-stranded extension, (ii) a sequence of at least 4 degenerate nucleotides, wherein the at least 4 degenerate nucleotide sequence is a random sequence that differs for each polynucleotide in a population of polynucleotides; and (iii) a site-specific cleavable sequence or nucleotide at or near the junction between the double-stranded region and the single-strand extension, suitable for removing the single-strand extension by cleavage;

wherein the partially double-stranded polynucleotide molecule is suitable for use as a 3' polynucleotide adapter.

2. The composition according to claim 1, wherein the bottom strand further comprises a blocking moiety at the 3' terminus.

3. The composition according to claim 1, wherein the top strand has a phosphorylated or pre-adenylated 5' terminus.

4. The composition according to claim 1, wherein the partially double-stranded polynucleotide is formed from a polynucleotide that is single-stranded.

5. The composition according to claim 1, wherein the partially double-stranded polynucleotide is formed from two polynucleotide strands.

6. The polynucleotide molecule of claim 1, wherein the polynucleotide molecule is a DNA.

7. The polynucleotide molecule of claim 1, wherein the polynucleotide molecule is RNA.

8. The polynucleotide molecule of claim 1, wherein the 3' single-stranded extension has a length in the range of 4-12 nucleotides.

9. The polynucleotide molecule of claim 1, wherein the site-specific cleavable sequence or nucleotide is a deoxyuridine.

10. The polynucleotide molecule of claim 1, wherein the site-specific cleavable sequence or nucleotide is a restriction endonuclease cleavage site.

11. The polynucleotide molecule of claim 2, wherein the blocking nucleotide prevents ligation.

12. The polynucleotide according to claim 2, wherein the blocking moiety comprises a modification selected from the group consisting of a 3' inverted dT, a 3' C3 spacer, a 3' amino dN, a 3' phosphorylated dN, and a dideoxynucleotide.

13. The polynucleotide molecule of claim 1, wherein the site-specific cleavable sequence or nucleotide is positioned at the junction of the single-stranded extension and the double-stranded region.

14. The polynucleotide molecule of claim 1, wherein the site-specific cleavable sequence or nucleotide is positioned within the double-stranded region on the bottom strand within 8 nucleotides of the junction of the single-stranded extension and the double-stranded region.

15. The polynucleotide according to claim 1, wherein there is more than one cleavable nucleotide or sequence in the polynucleotide molecule, wherein each of the cleavable nucleotides or sequences is positioned in the double-stranded region on the bottom strand within 8 nucleotides of the junction of the single-stranded extension and the double-stranded region.

16. A kit comprising:
(a) a partially double-stranded polynucleotide molecule according to claim 1; and
(b) a second polynucleotide molecule comprising a top strand and a bottom strand, wherein the top strand comprises or consists of a nucleic acid sequence that is complementary to a portion of the nucleic acid sequence of the bottom strand, such that the top strand and bottom strand form a double-stranded region by complementary base-pairing, and wherein the bottom strand comprises a 5' single-stranded extension with a sequence containing at least 4 degenerate nucleotides, wherein the sequence containing the at least 4 degenerate nucleotide sequence is a random sequence that differs for each polynucleotide in a population of polynucleotides.

17. The kit according to claim 16, further comprising one or more enzymes selected from the group consisting of a ligase, a nicking endonuclease, a glycosylase, a deadenylase, and an exonuclease.

18. A kit comprising:
(a) a polynucleotide molecule according to claim 1, for use as a 3' adapter; and
(b) one or more enzymes selected from the group consisting of a ligase, a nicking endonuclease, a glycosylase, a deadenylase, and an exonuclease.

19. The kit according to claim 18, further comprising a second polynucleotide molecule for use as a 5' adapter, comprising: a top strand and a bottom strand, wherein (i) the top strand comprises a nucleic acid sequence that is complementary to a portion of the nucleic acid sequence of the bottom strand, (ii) the bottom strand comprises a 5' single-stranded extension a sequence of at least 4 degenerate nucleotides and optionally a blocking moiety at the 5' terminus, wherein the at least 4 degenerate nucleotide sequence is a random sequence that differs for each polynucleotide in a population of polynucleotides; (iii) a site-specific cleavable sequence or nucleotide at or near the junction between the double-stranded region and the single-strand extension, suitable for removing the single-strand extension by cleavage, and optionally; (iv) the first polynucleotide molecule is DNA for ligating to a 5' end of a target polynucleotide and the second polynucleotide molecule is an RNA for ligating to the 5' end of the target polynucleotide molecule.

20. A method ligating a 3' polynucleotide adapter to a population of target polynucleotides, comprising:
(a) using the polynucleotide molecule of claim 1 as a 3' adapter;
(b) combining the 3' adapter with a population of target polynucleotides to produce a reaction mix;
(c) incubating the reaction mix to ligate the 3' adapter to the 3' of the target polynucleotides; and
(d) cleaving the 3' adapter at the site-specific cleavable sequence or nucleotide after step (c) so as to remove the degenerate sequence.

21. The method according to claim 20, wherein the 3' adapter is DNA and the target polynucleotide is RNA.

22. The method of claim 21, further comprising:
(e) adding a 5' adapter molecule having a 5' single-strand extension comprising degenerate nucleotides to the product of step (c) to produce a second reaction mix; and
(f) incubating the second reaction mix to ligate the 5' polynucleotide adapter to the RNA molecules.

23. The method according to claim 22, wherein the 5' adapter is RNA.

24. The method according to claim 22, wherein steps (a)(f) are performed in a single reaction vessel.

25. The method according to claim 22, wherein no intermediate purification or separation steps are performed between steps (a)-(f).

26. The method according to claim 20, further comprising incubating the product of step (f) with a reverse transcriptase, to copy the ligated RNA into cDNA.

27. The method according to claim 26, wherein cDNA synthesis is primed using the bottom strand of the polynucleotide molecule, after the 3' single-stranded extension has been cleaved.

28. The method according to claim 20, wherein adapter ligation yield and bias does not vary significantly for other populations of RNA.

29. The method according to claim 20, wherein the RNA molecules are variable in size and concentration.

30. A partially double-stranded polynucleotide molecule comprising a double-stranded region having a first nucleic acid strand and a second complementary nucleic acid strand, wherein:
(i) the first and second strands are a portion of one or comprise 2 polynucleotide molecules;
(ii) the first nucleic acid strand optionally comprises one or more of a phosphorylated or pre-adenylated at the 5' terminus and a blocking moiety at the 3' terminus;
(iii) the second complementary strand having a nucleic acid sequence that extends 3' from the double-stranded region to form a single-stranded extension containing at least 4 degenerate nucleotides in a sequence that wherein the sequence differs for each polynucleotide in a population of polynucleotides; and
(iv) a site-specific cleavable sequence or nucleotide at or near the junction between the double-stranded region and the single-strand extension, suitable for removing the single-strand extension by cleavage.

* * * * *